United States Patent
Hsu et al.

(10) Patent No.: US 10,004,719 B1
(45) Date of Patent: Jun. 26, 2018

(54) SOLID DISPERSION FORMULATION

(71) Applicant: TaiGen Biotechnology Co., Ltd., Taipei (TW)

(72) Inventors: Ming-Chu Hsu, Glendora, CA (US); Chu-Chung Lin, Taipei (TW); Chi-Hsin Richard King, Des Peres, MO (US)

(73) Assignee: TaiGen Biotechnology Co., Ltd., Taipei (TW)

( * ) Notice: Subject to any disclaimer, the term of this patent is extended or adjusted under 35 U.S.C. 154(b) by 0 days. days.

(21) Appl. No.: 15/607,825

(22) Filed: May 30, 2017

(51) Int. Cl.
| | |
|---|---|
| C07D 473/00 | (2006.01) |
| C07D 473/34 | (2006.01) |
| C07D 471/04 | (2006.01) |
| A61K 31/407 | (2006.01) |
| A61K 31/79 | (2006.01) |
| A61K 31/795 | (2006.01) |
| A61K 31/765 | (2006.01) |
| A61K 31/4015 | (2006.01) |
| A61K 31/41 | (2006.01) |
| A61K 9/14 | (2006.01) |
| A61K 9/20 | (2006.01) |

(52) U.S. Cl.
CPC ........ *A61K 31/407* (2013.01); *A61K 31/4015* (2013.01); *A61K 31/41* (2013.01); *A61K 31/765* (2013.01); *A61K 31/79* (2013.01); *A61K 31/795* (2013.01); *A61K 9/14* (2013.01); *A61K 9/20* (2013.01); *A61K 2300/00* (2013.01)

(58) Field of Classification Search
CPC ... C07D 473/00; C07D 473/34; C07D 471/04
See application file for complete search history.

(56) References Cited

U.S. PATENT DOCUMENTS

| | | | |
|---|---|---|---|
| 8,389,560 B2 | 3/2013 | Liu et al. | |
| 9,738,629 B2 * | 8/2017 | Zhang | C07D 403/14 |
| 2011/0312973 A1 | 12/2011 | Liepold et al. | |
| 2014/0212487 A1 | 7/2014 | Mogalian et al. | |
| 2017/0087174 A1 | 3/2017 | Beumont et al. | |

OTHER PUBLICATIONS http://alveice.blogspot.tw/2015/05/ctg-2349-furaprevir-merck-grazoprevir.html "A Phase 2, Multicenter, Randomized, Open-label, Dose-ranging Study to Evaluate the Efficacy and Safety of TG-2349 in Combination with Peg-interferon and Ribavirin in Treatment Naïve East Asian Subjects with Chronic Hepatitis C Virus Genotype 1b Infection." May 24, 2015.

* cited by examiner

*Primary Examiner* — Sun Jae Yoo
(74) *Attorney, Agent, or Firm* — Cesari and McKenna, LLP

(57) ABSTRACT

A spray-dried solid dispersion containing a pharmaceutical compound of formula (I) shown below and a pharmaceutically acceptable polymer,

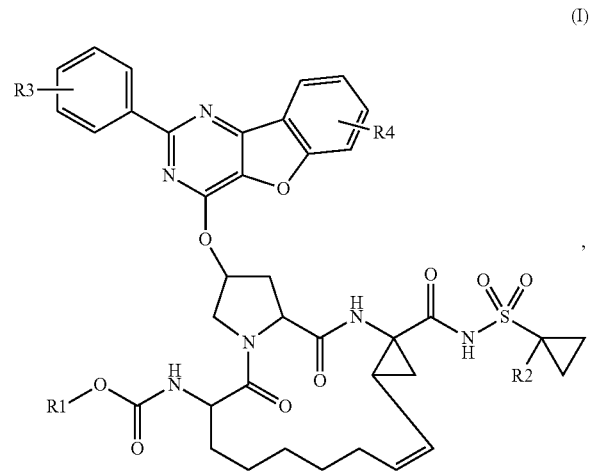

in which the pharmaceutical compound is dispersed in a polymer matrix formed from the pharmaceutically acceptable polymer. Further disclosed are methods for preparing such a solid dispersion and using it for treating hepatitis C virus infection and a pharmaceutical formulation containing same.

29 Claims, 1 Drawing Sheet

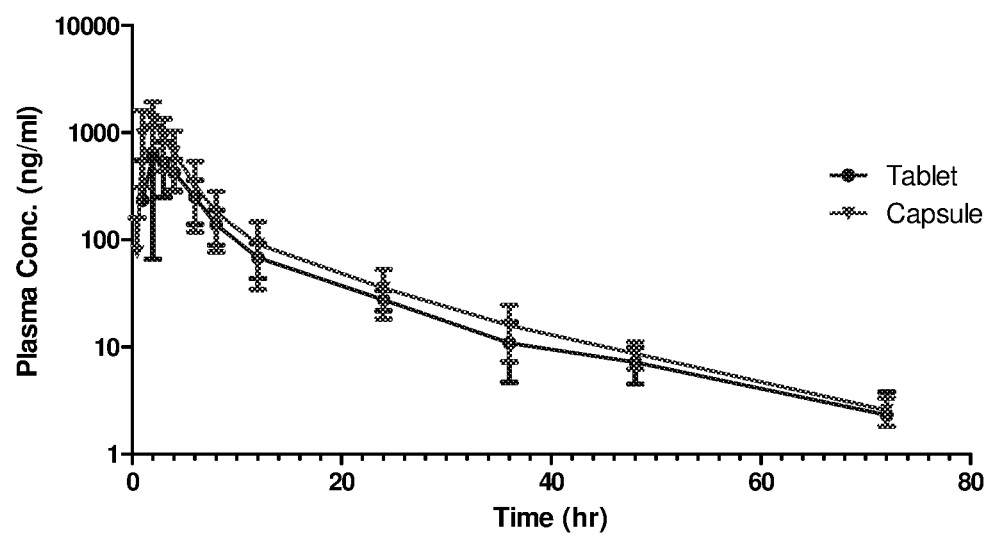

SOLID DISPERSION FORMULATION

FIELD OF THE INVENTION

The present invention relates to a spray-dried solid dispersion containing a macrocyclic compound and methods of preparing and using the solid dispersion for treating hepatitis C virus infection.

BACKGROUND

Hepatitis C virus (HCV) infection is difficult to treat as it can quickly mutate and escape the natural immune response. The HCV genome, containing a single polyprotein of about 3000 amino acids, includes a nucleocapsid protein, envelope proteins (E1 and E2), and several non-structural proteins (p7, NS2, NS3, NS4A, NS5A, and NS5B). Among these proteins, the NS3 protein possesses serine protease activity and is considered essential for viral replication and infectivity. HCV NS3 protease, which facilitates proteolysis at the NS3/NS4A, NS4A/NS4B, NS4B/NS5A, NS5A/NS5B junctions, is responsible for generating four viral proteins during viral replication. Consequently, the HCV NS3 protease is an attractive target in treating HCV infection.

Certain macrocyclic compounds have demonstrated a potential for inhibiting NS3/4A proteases activity, decreasing HCV RNA levels, and inhibiting HCV protease mutants that are resistant to various HCV inhibitors. See Liu et al., U.S. Pat. No. 8,389,560. On the other hand, these compounds exhibit poor pharmacological properties, e.g., low solubility and low bioavailability, thereby restricting their use as effective therapeutics for treating HCV infection.

There is a need to develop new formulations that contain these macrocyclic compounds yet do not have the above-described drawbacks.

SUMMARY

An aspect of the present invention is a spray-dried solid dispersion that unexpectedly exhibits high solubility and high bioavailability.

The spray-dried solid dispersion contains a pharmaceutically acceptable polymer and a pharmaceutical compound or a pharmaceutically acceptable salt thereof, in which the pharmaceutical compound or its salt is dispersed in a polymer matrix formed from the pharmaceutically acceptable polymer.

In the spray-dried solid dispersion, the weight ratio of the pharmaceutical compound to the pharmaceutically acceptable polymer is from 4:1 to 1:4, and the pharmaceutically acceptable polymer is poloxamer, polyvinylpyrrolidone, or hydroxypropylcellulose.

The pharmaceutical compound has formula (I) as shown below:

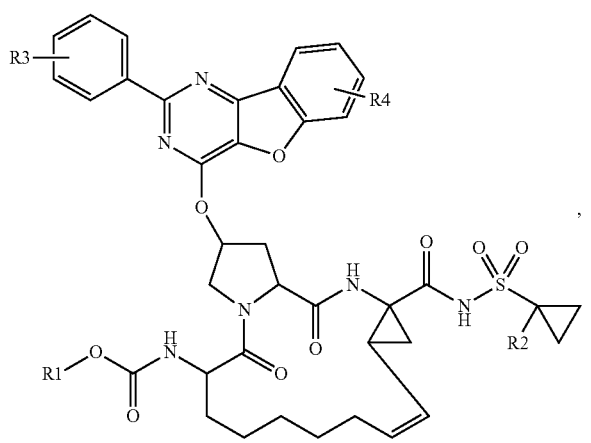

(I)

in which R1 is H, $C_{1-6}$ alkyl, $C_{3-10}$ cycloalkyl, $C_{3-10}$ heterocycloalkyl, aryl, or heteroaryl, each of $C_{1-6}$ alkyl, $C_{3-10}$ cycloalkyl, $C_{3-10}$ heterocycloalkyl, aryl, and heteroaryl being optionally mono-, di-, or tri-substituted with halo, nitro, cyano, amino, $C_{1-6}$ alkyl, $C_{1-6}$ alkoxyl, $C_{2-6}$ alkenyl, $C_{2-6}$ alkynyl, aryl, or heteroaryl; R2 is H, halo, or $C_{1-6}$ alkyl; R3 is H, halo, nitro, cyano, amino, $C_{1-6}$ alkyl, $C_{1-6}$ alkoxyl, $C_{2-6}$ alkenyl, $C_{2-6}$ alkynyl, $C_{3-10}$ cycloalkyl, $C_{3-10}$ heterocycloalkyl, aryl, or heteroaryl, or R3 is fused with phenyl to form a bicycle, each of amino, $C_{1-6}$ alkyl, $C_{1-6}$ alkoxyl, $C_{2-6}$ alkenyl, $C_{2-6}$ alkynyl, aryl, and heteroaryl being optionally mono-, di-, or tri-substituted with halo; and R4 is H, halo, nitro, cyano, amino, $C_{1-6}$ alkyl, $C_{1-6}$ alkoxyl, $C_{2-6}$ alkenyl, $C_{2-6}$ alkynyl, $C_{3-10}$ cycloalkyl, $C_{3-10}$ heterocycloalkyl, aryl, or heteroaryl, each of amino, $C_{1-6}$ alkyl, $C_{1-6}$ alkoxyl, $C_{2-6}$ alkenyl, $C_{2-6}$ alkynyl, $C_{3-10}$ cycloalkyl, $C_{3-10}$ heterocycloalkyl, aryl, and heteroaryl being optionally mono-, di-, or tri-substituted with halo, nitro, cyano, amino, $C_{1-6}$ alkyl, $C_{1-6}$ alkoxyl, $C_{2-6}$ alkenyl, $C_{2-6}$ alkynyl, aryl, or heteroaryl.

A subset of the compounds described above feature that R1 is $C_{1-6}$ alkyl or $C_{3-10}$ cycloalkyl; R2 is H or $C_{1-6}$ alkyl; R3 is H, halo, amino, $C_{1-6}$ alkyl, or $C_{1-6}$ alkoxyl, each of the amino, $C_{1-6}$ alkyl, and $C_{1-6}$ alkoxyl being optionally mono-, di-, or tri-substituted with halo; and R4 is H, halo, $C_{1-6}$ alkyl, or $C_{1-6}$ alkoxyl.

The term "alkyl" herein refers to a saturated, linear, or branched hydrocarbon moiety, e.g., —$CH_3$ or —$CH(CH_3)_2$. The term "alkoxy" refers to an —$O(C_{1-6}$ alkyl) radical, e.g., —$OCH_3$ and —$OCH(CH_3)_2$. The term "alkenyl" refers to a linear or branched hydrocarbon moiety that contains at least one double bond, e.g., —CH=CH—$CH_3$. The term "alkynyl" refers to a linear or branched hydrocarbon moiety that contains at least one triple bond, e.g., —C≡C—$CH_3$. The term "cycloalkyl" refers to a saturated, cyclic hydrocarbon moiety, e.g., cyclohexyl. The term "heterocycloalkyl" refers to a saturated, cyclic moiety having at least one ring heteroatom (e.g., N, O, and S), e.g., 4-tetrahydropyranyl. The term "aryl" refers to a hydrocarbon moiety having one or more aromatic rings. Examples of aryl include phenyl (Ph), phenylene, naphthyl, naphthylene, pyrenyl, anthryl, and phenanthryl. The term "heteroaryl" refers to a moiety having one or more aromatic rings that contain at least one heteroatom (e.g., N, O, and S). Examples of heteroaryl include furyl, furylene, fluorenyl, pyrrolyl, thienyl, oxazolyl, imidazolyl, thiazolyl, pyridyl, pyrimidinyl, quinazolinyl, quinolyl, isoquinolyl, and indolyl. The term "amino" refers to a radical of —$NH_2$, —$NH(C_{1-6}$ alkyl), or —$N(C_{1-6}$ alkyl)$_2$, e.g., —$NHCH_3$ and —$NHCH(CH_3)_2$. The term "halo" refers to fluoro, chloro, bromo, or iodo.

Alkyl, alkenyl, alkynyl, cycloalkyl, heterocycloalkyl, aryl, and heteroaryl mentioned herein include both substituted and unsubstituted moieties, unless specified otherwise. Possible substituents on cycloalkyl, heterocycloalkyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ heterocycloalkyl, $C_1$-$C_{10}$ alkoxy, aryl, aryloxy, heteroaryl, heteroaryloxy, amino, $C_1$-$C_{20}$ alkylamino, dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amidino, guanidine, ureido, cyano, nitro, nitroso, azido, acyl, thioacyl, acyloxy, carboxyl, and carboxylic ester. On the other hand, possible substituents on alkyl, alkenyl, or alkynyl include all of the above-recited substituents except $C_1$-$C_{10}$ alkyl. Cycloalkyl, heterocycloalkyl, aryl, and heteroaryl can also be fused with each other.

The compounds described above include the compounds themselves, as well as their salts, prodrugs, polymorphs, stereoisomers and solvates, if applicable. A salt, for example, can be formed between an anion and a positively charged group (e.g., amino) on a compound having one of the above formulas. Suitable anions include chloride, bromide, iodide, sulfate, nitrate, phosphate, citrate, methanesulfonate, trifluoroacetate, acetate, malate, tosylate, tartrate, fumarate, glutamate, glucuronate, lactate, glutarate, and maleate. Likewise, a salt can also be formed between a cation and a negatively charged group (e.g., carboxylate) on a compound having one of the above formulas. Suitable cations include sodium ion, potassium ion, magnesium ion, calcium ion, and an ammonium cation such as tetramethylammonium ion. The compounds also include those salts containing quaternary nitrogen atoms. For calculation simplicity, unless otherwise stated, the weight of a compound mentioned herein refers to that of the free base form of that compound. Examples of prodrugs include esters and other pharmaceutically acceptable derivatives, which, upon administration to a subject, are capable of providing active compounds. A solvate refers to a complex formed between an active compound and a pharmaceutically acceptable solvent. Examples of pharmaceutically acceptable solvents include water, ethanol, isopropanol, ethyl acetate, acetic acid, and ethanolamine.

Examples of a pharmaceutical compound to be contained in a spray-dried solid dispersion of this invention include, but are not limited to, the compounds shown below:

Compound 1

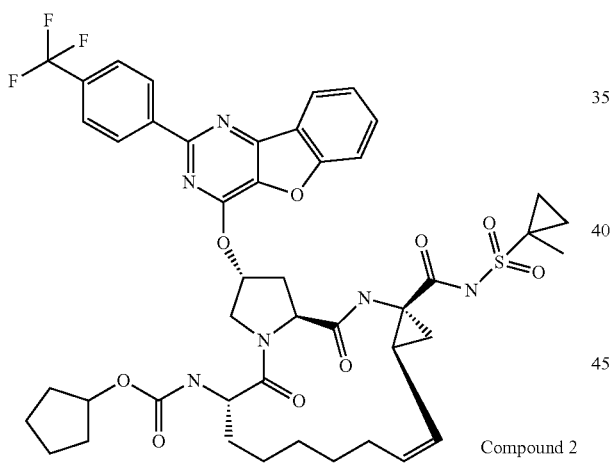

Compound 2

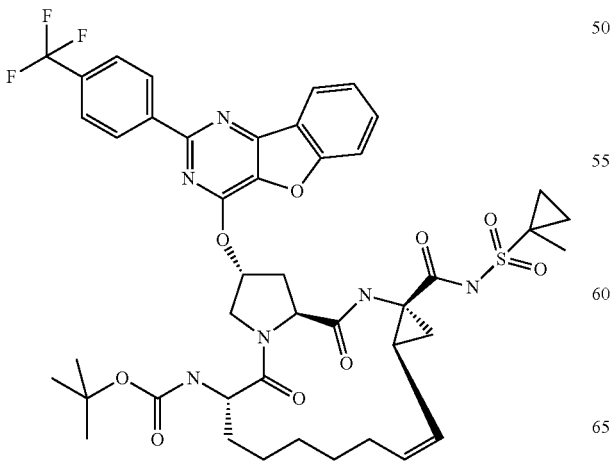

Compound 3

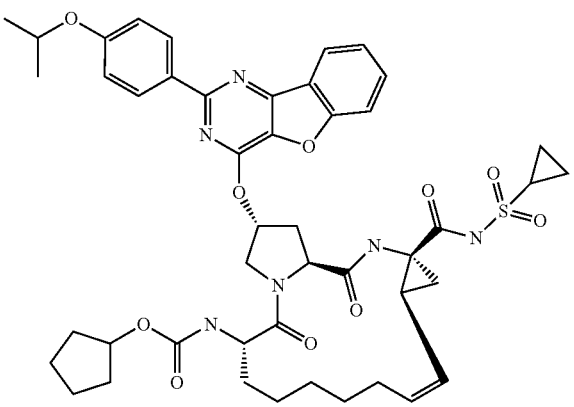 [SMILES: CC(C)Oc1ccc(-c2nc(O[C@@H]3C[C@H]4C(=O)N[C@]5(C(=O)NS(=O)(=O)C6(C)CC6)C[C@H]5/C=C\CCCCC[C@H](NC(=O)OC5CCCC5)C(=O)N4C3)c3oc4ccccc4c3n2)cc1]

Compound 4

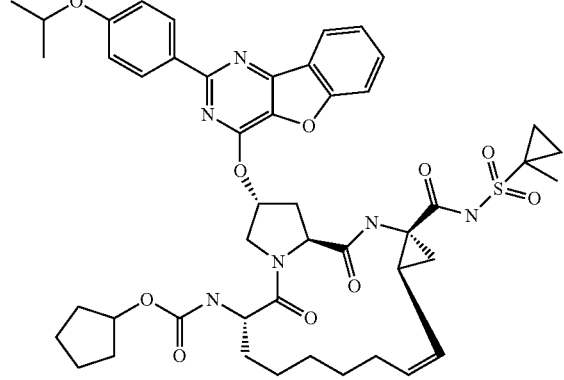

Compound 5

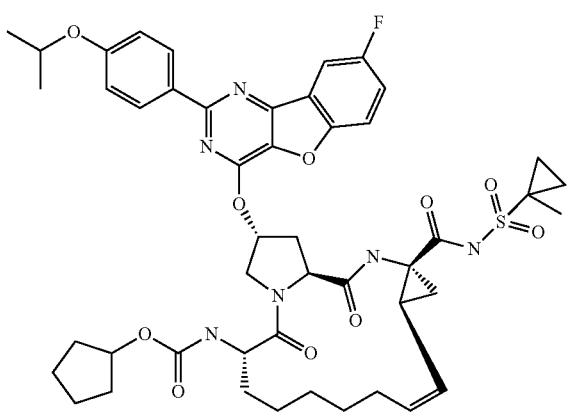

Compound 6
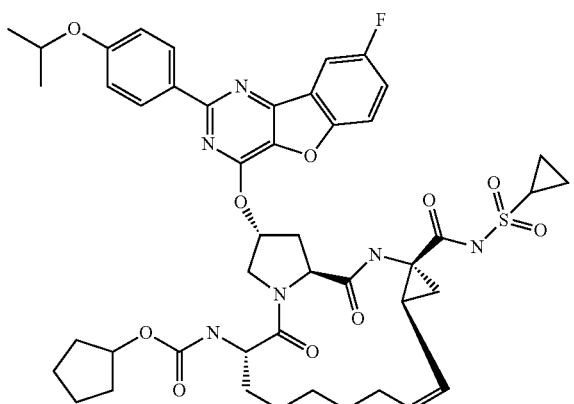
Compound 7
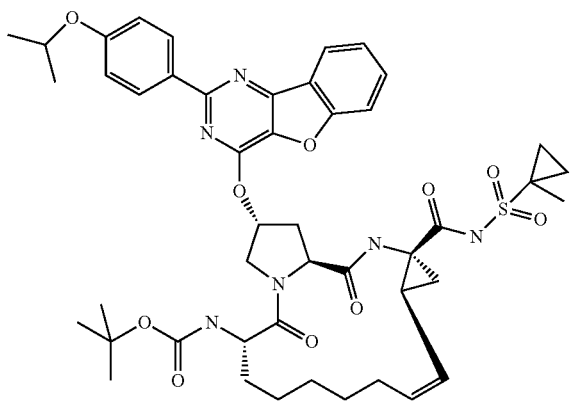
Compound 8
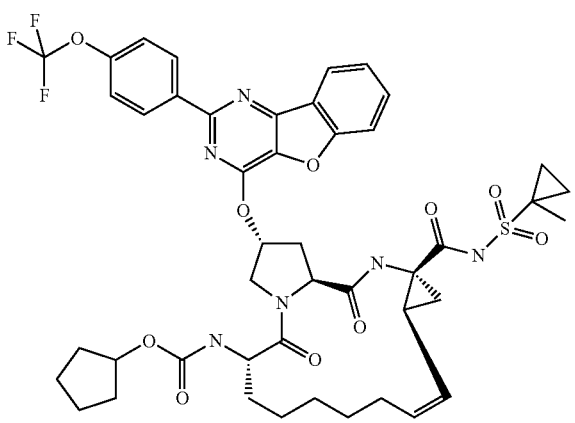
Compound 9
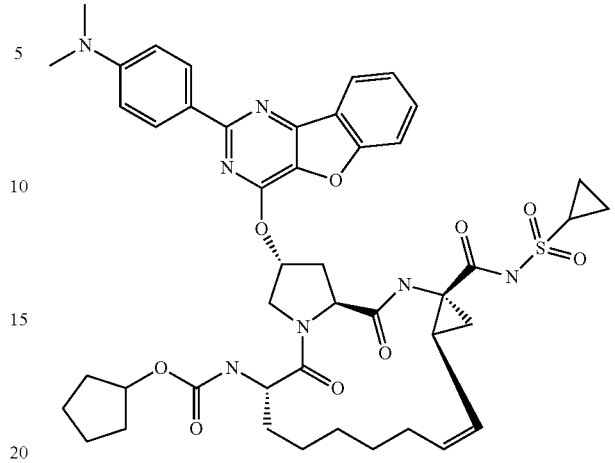
Compound 10
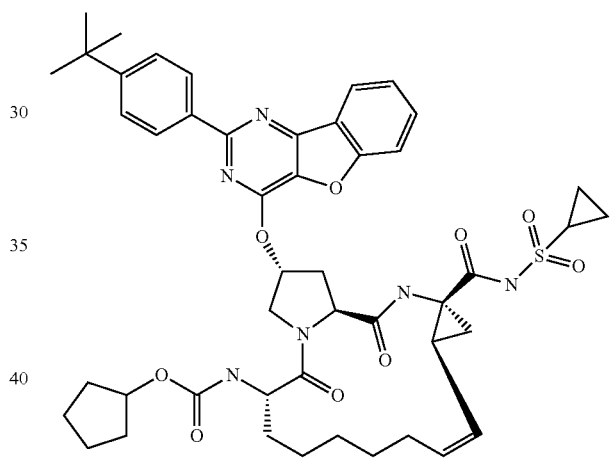
Compound 11
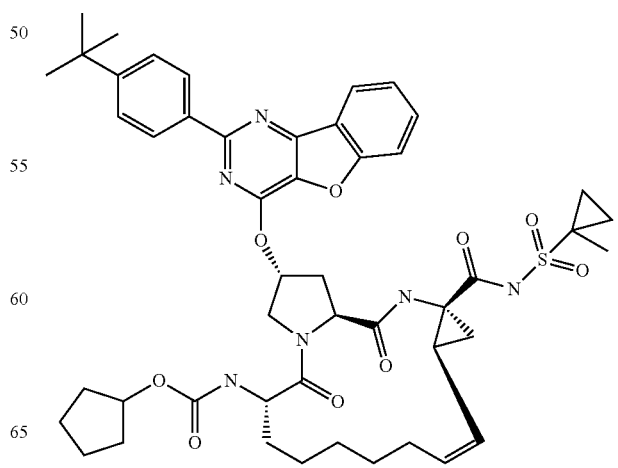

Compound 12

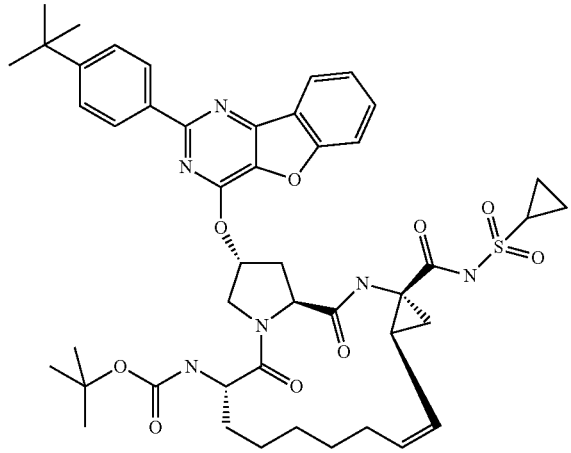

Compound 13

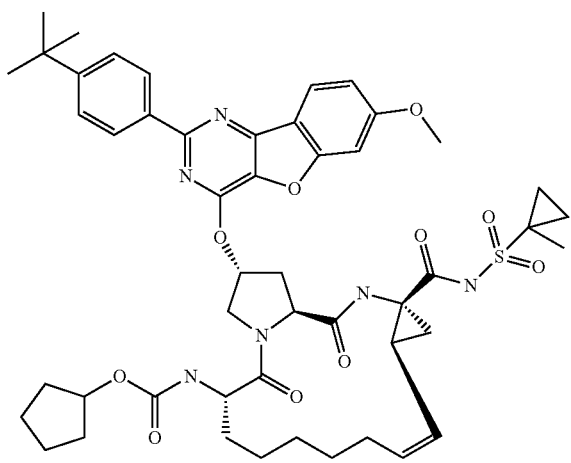

Compound 14

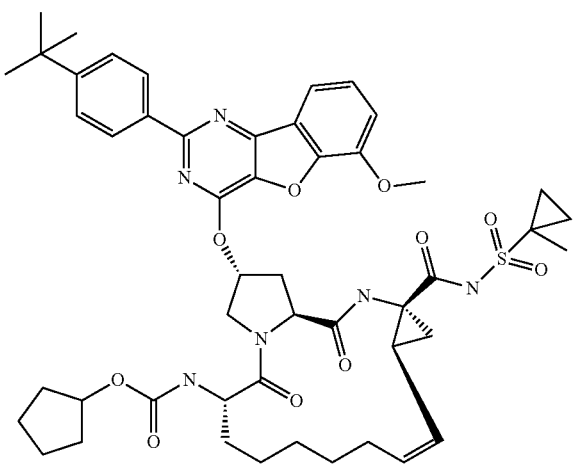

The pharmaceutical compound contained in a spray-dried solid dispersion can be substantially amorphous.

An exemplary spray-dried solid dispersion contains the following compound:

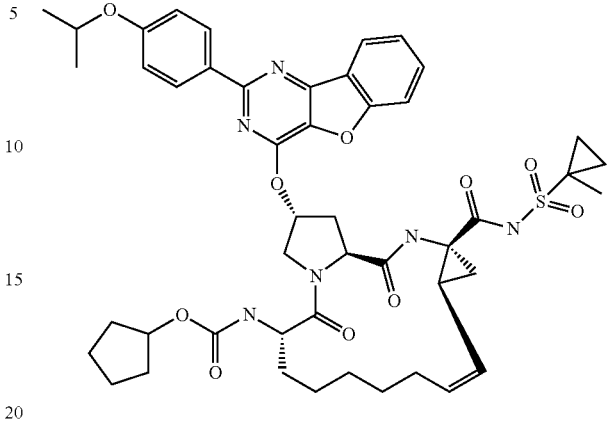

Another aspect of this invention is a pharmaceutical formulation containing a spray-dried solid dispersion described above and optionally one or more pharmaceutical acceptable ingredients. The pharmaceutical acceptable ingredients are diluents, disintegrants, binders, lubricants, glidants, surfactants, or a combination thereof.

In the pharmaceutical formulation, the spray-dried solid dispersion can be present at 30% to 80% w/w (e.g., 60% to 70% w/w). Typically, the formulation is produced in unit dosage form and contains one of the above-described pharmaceutical compounds in an amount of 50 to 400 mg (e.g., 50 to 250 mg, 50 mg, and 100 mg).

An exemplary pharmaceutical formulation contains a spray-dried solid dispersion present at 60% to 70% w/w, in which the pharmaceutical compound is

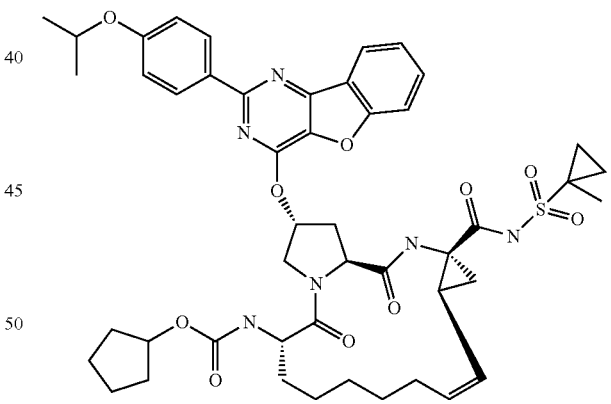

and the weight ratio of the compound to the pharmaceutically acceptable polymer is from 2:1 to 1:2.

A further aspect of this invention is a method of making the spray-dried solid dispersion described above.

The method includes the steps of mixing the compound and the pharmaceutically acceptable polymer in a solvent to provide a feeder solution and spray-drying the feeder solution to afford a spray-dried solid dispersion.

Also within the scope of this invention is a method of using a spray-dried solid dispersion or a pharmaceutical formulation containing the spray-dried solid dispersion for treating HCV infection in a human in need thereof. The method includes administering to the human a therapeutically effective amount of the spray-dried solid dispersion or a pharmaceutical formulation containing the same.

The details of the invention are set forth in the description below. Other features, objects, and advantages of the invention will be apparent from the following drawing and detailed description of several embodiments, and also from the appending claims.

BRIEF DESCRIPTION OF THE DRAWING

FIG. 1 is a schematic depiction of the plasma concentration versus time curves from dosing in beagle dogs a tablet and a capsule formulation of this invention.

DETAILED DESCRIPTION

Disclosed first in detail herein is a spray-dried solid dispersion for forming a pharmaceutical formulation.

As described above, the spray-dried solid dispersion contains a pharmaceutically acceptable polymer and a compound of formula (I) shown below or a pharmaceutically acceptable salt thereof:

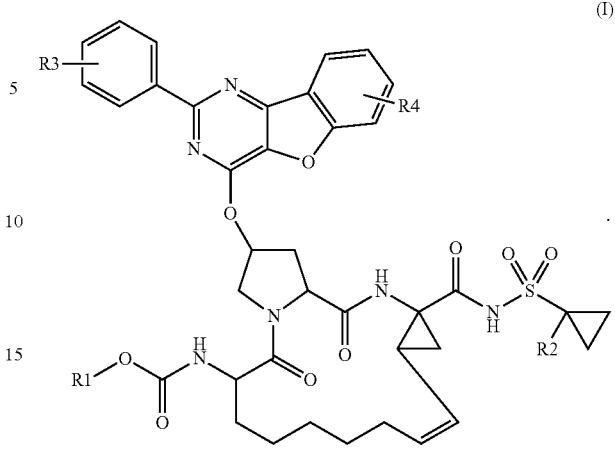

Variables R1-R4 are defined as described in the SUMMARY section.

The compounds of formula (I) can be synthesized from commercially available starting materials by following the synthetic route shown in Scheme 1 below.

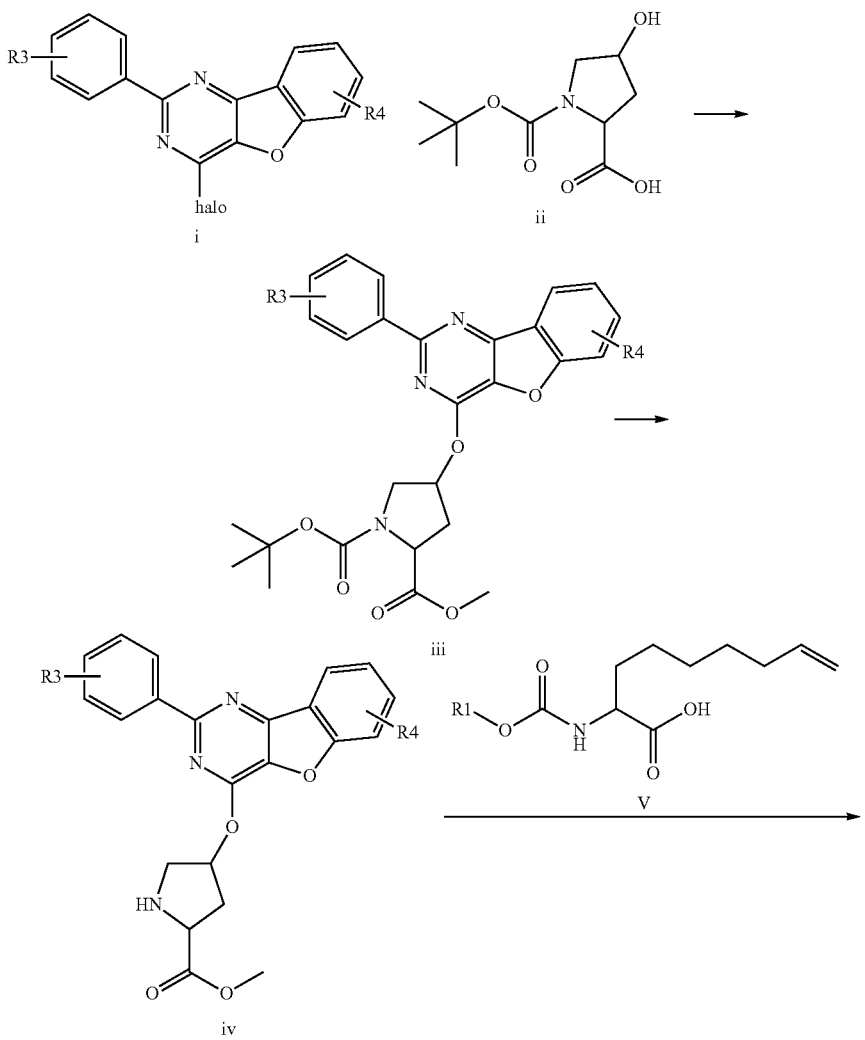

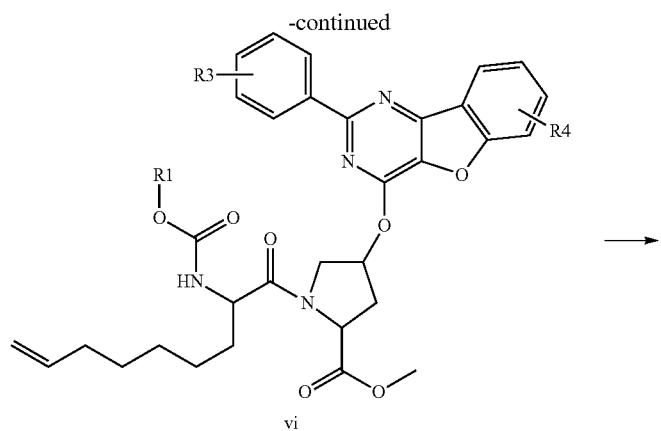
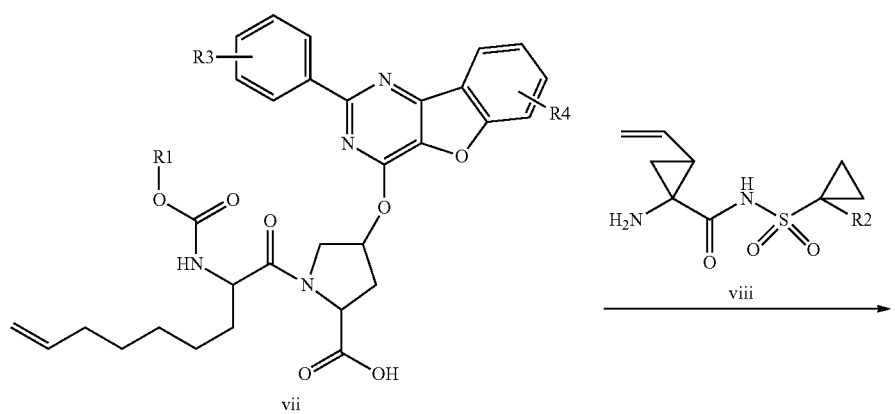
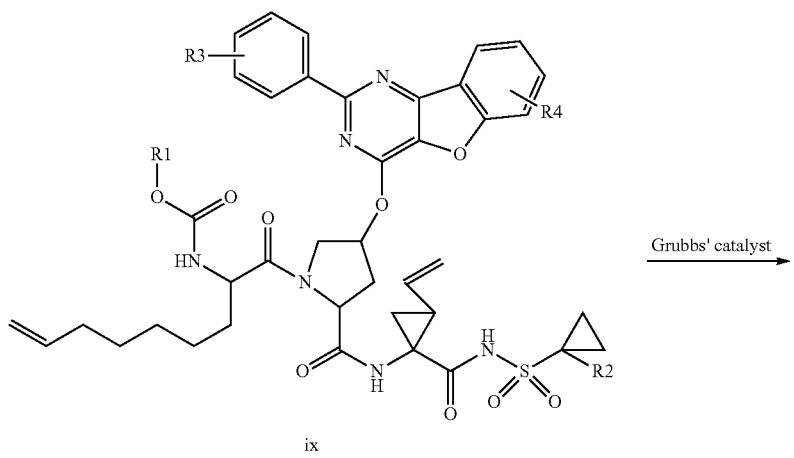

-continued

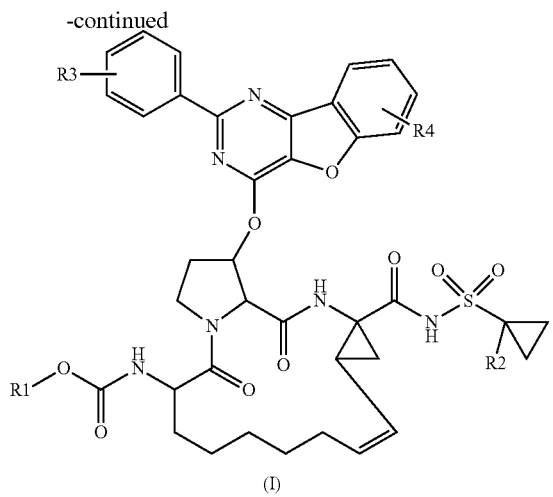

(I)

As illustrated in Scheme 1, halo-substituted heteroaryl compound (i) is first coupled with N-(t-butoxycarbonyl)-L-proline (ii), followed by methylation, to form intermediate (iii). Intermediate (iii) is then deprotected to remove the N-butoxycarbonyl group to produce free amino compound (iv), which is subsequently coupled with carboxylic acid (v) to afford intermediate (vi). Intermediate (vi) is hydrolyzed to give acid (vii), which is coupled with amine compound (viii) to provide pyrrolidine compound (ix) having two terminal alkenyl groups. Intermediate (ix) undergoes olefine metathesis in the presence of Grubbs' catalyst to afford desired a macrocyclic compound having formula (I).

The synthesis described above can also include additional steps, either before or after the steps shown in Scheme 1, to add or remove suitable protecting groups in order to ultimately allow synthesis of various compounds. In addition, various synthetic steps may be performed in an alternate sequence or order to give certain compounds. Synthetic chemistry transformations and protecting group methodologies (protection and de-protection) useful in synthesizing applicable compounds of formula (I) are known in the art and include, for example, those described in R. Larock, Comprehensive Organic Transformations, VCH Publishers (1989); T. W. Greene and P. G. M. Wuts, Protective Groups in Organic Synthesis, 2$^{nd}$ Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995) and subsequent editions thereof.

The compounds mentioned herein contain a non-aromatic double bond and asymmetric centers. Thus, they can occur as racemates and racemic mixtures, single enantiomers, individual diastereomers, diastereomeric mixtures, tautomers, and cis- or trans-isomeric forms. All such isomeric forms are contemplated.

To practice this invention, one can prepare a solid dispersion that contains a compound of formula (I) and a pharmaceutically acceptable polymer. Compounds of formula (I) generally have low aqueous solubility, and their absorption in vivo is dissolution-rate limited. A solid dispersion containing a compound of formula (I) can increase the compound solubility/dissolution, thereby improving the bioavailability of the compound of formula (I).

The term "solid dispersion" herein refers to the dispersion of a pharmaceutically active ingredient, e.g., a compound of formula (I), in an inert polymer matrix at solid state. A solid dispersion can be prepared by methods well known in the art, e.g., spray-drying or hot-melt extrusion. The matrix can be either crystalline or amorphous. A solid dispersion contains a co-precipitate of a pharmaceutically active ingredient and one or more water-soluble polymers, in which the pharmaceutically active ingredient is dispersed uniformly within a polymer matrix formed from the polymers. The pharmaceutically active ingredient can be present in an amorphous state, a crystalline dispersed form, or a combination thereof. It can also be finely dispersed or dissolved as single molecules in the polymer matrix. The solid dispersion is typically prepared by a spray-drying method or a hot-melt extrusion method. The solid dispersion of this invention is prepared by the spray-drying method.

The method for preparing the solid dispersion of this invention includes steps of (i) mixing a compound of formula (I) and a polymer in an organic solvent to provide a feeder solution and (ii) spray-drying the feeder solution through a nozzle as a fine spray into a chamber where the solvent is evaporated quickly to generate particles containing the compound and polymer. Following formation of a solid dispersion, the resulting spray-dried particle can undergo a secondary drying step to remove residual solvents. The secondary drying step can take place in a static dryer or an agitated dryer. Gas, humidified gas, vacuum can be applied to the secondary drying step and such application is useful in more rapidly removing residual solvents that remain in the spray-dried particle.

Any organic solvent that can easily dissolve or disperse the compound of formula (I) and the polymer described above can be used. Examples of the organic solvent include lower carbon-number alcohols, e.g., methanol, ethanol, propanol, and isopropanol; ketones, e.g., methylethyl ketone and butanone; and a combination thereof.

The polymer used in the spray-dried method can be a homopolymer of N-vinyl pyrrolidone, a copolymer of N-vinyl pyrrolidone, a copolymer of N-vinyl pyrrolidone and vinyl acetate, a copolymer of N-vinyl pyrrolidone and vinyl propionate, polyvinylpyrrolidone, methylcellulose, ethylcellulose, a hydroxyalkylcellulose (e.g., hydroxyethylcellulose, hydroxypropylcellulose, hydroxyalkylalkylcellulose, and hydroxypropylmethylcellulose), cellulose phthalate, cellulose succinate, cellulose acetate phthalate, hydroxypropylmethylcellulose phthalate, hydroxypropylmethylcellulose succinate, hydroxypropylmethylcellulose acetate succinate, polyethylene oxide, polypropylene oxide, copolymer of ethylene oxide and propylene oxide, methacrylic acid/ethyl acrylate copolymer, methacrylic acid/methyl methacrylate copolymer, butyl methacrylate/2-dimethylaminoethyl methacrylate copolymer, polyethylene oxide, polyethylene glycol, poly(hydroxyalkyl acrylate), poly(hydroxyalkyl methacrylate), copolymer of vinyl acetate and crotonic acid, partially hydrolyzed polyvinyl acetate, carrageenan, galactomannan, or xanthan gum.

Typically, the polymer used in forming the solid dispersion is a hydrophilic polymer. Examples of a hydrophilic polymer include polyvinylpyrrolidone (e.g., PVP VA64 and PVP K30), hydroxypropylcellulose (e.g., HPC-L and HPC-SSL), and poloxamer (e.g., poloxamer 188).

In one embodiment, the polymer is one of poloxamer 188, PVP VA64, PVP K30, HPC-L, and HPC-SSL.

In another embodiment, the polymer is one of poloxamer 188, PVP K30, HPC-L, and HPC-SSL In still another embodiment, the polymer is HPC-SSL or PVP K30.

In a further embodiment, the polymer is HPC-SSL.

The weight ratio of the compound of formula (I) to the polymer contained in a solid dispersion is typically from about 4:1 to about 1:4, which is expressed as compound:polymer or drug:polymer. It can be about 3:1 to about 1:3, about 2:1 to about 1:2, about 1.5:1 to about 1:1.5, about 2:1 to about 1:1, about 1:1 to about 1:2, about 1.5:1 to about 1:1, or about 1:1 to about 1:1.5. For example, the weight ratio of compound to polymer is about 2:1, 1.9:1, 1.8:1, 1.7:1, 1.6:1, 1.5:1, 1.4:1, 1.3:1, 1.2:1, 1:1, 1:1.1, 1:1.2, 1:1.3, 1:1.4, 1:1.5, 1:1.6, 1:1.7, 1:1.8, 1:1.9, or 1:2.

The spray-dried solid dispersion described above can be administered orally to a subject (e.g., a human) in need thereof to exert a therapeutic effect, e.g., treating HCV infection.

Also within the scope of this invention is a pharmaceutical formulation that contains a spray-dried solid dispersion and optionally one or more pharmaceutically acceptable ingredients.

The term "pharmaceutically acceptable ingredient" herein refers to an inert additive used to prepare a solid formulation, e.g., a powder, a granule, a capsule, a pellet, and a tablet, to increase the bulk of the desired formulation containing the spray-dried solid dispersion described above. The pharmaceutically acceptable ingredients can be added during or after the preparation of spray-dried form of the solid dispersion. Examples of the pharmaceutically acceptable ingredients include diluents, fillers, bulking agents, binders, disintegrants, surfactants, lubricants, glidants, sweeteners, taste masking agents, colorants, and flavors.

Suitable diluents, fillers, and bulking agents include, but are not limited to, microcrystalline cellulose, di- or tri-basic calcium phosphate, crystalline cellulose, powdered cellulose, calcium carbonate, calcium sulphate, magnesium silicate, magnesium trisilicate, magnesium aluminium metasilicate, kaolin, starch, starch derivatives, magnesium carbonate, magnesium oxide, and co-processed insoluble ingredients.

Suitable disintegrants include, but are not limited to, croscarmellose sodium (CC-Na), microcrystalline cellulose (e.g., MCC 101 and MCC 102), crospovidone, cellulose, kaolin, crosslinked carboxy methyl cellulose (e.g., AcDiSol), crosslinked polyvinyl pyrrolidone (e.g., Kollidon CL), and a combination thereof. The amount of disintegrants in the pharmaceutical formulation ranges from about 10% to about 40% (e.g., about 20% to about 35% and about 28% to about 32%) by total weight of the formulation.

Suitable surfactants include, but are not limited to, an anionic, cationic, non-ionic, or amphoteric surfactant. An exemplary anionic surfactant is sodium lauryl sulfate (SLS). The amount of a surfactant present in the pharmaceutical formulation ranges from about 0.1% to about 2.5%, or about 0.5% to about 2% by total weight of the formulation.

Suitable lubricants and glidants include, but are not limited to, a stearic acid and its derivatives (e.g., sodium stearate, magnesium stearate and calcium stearate), sodium stearyl fumarate, and talc or colloidal silicon dioxide (CSD). The amount of lubricants or glidants present in the pharmaceutical composition ranges from about 0.1% to about 5% (e.g., about 0.5% to about 4% and about 1% to about 3%) by total weight of the formulation.

The active pharmaceutical ingredient can be present in the pharmaceutical formulation in a therapeutically effective amount. Typically, the pharmaceutical formulation contains a spray-dried solid dispersion present at about 30% to about 80% w/w (e.g., about 40% to about 70% w/w, about 50% to about 70% w/w, and about 60% to about 70% w/w). An exemplary pharmaceutical formulation contains about 63% w/w of a spray-dried solid dispersion. Another exemplary pharmaceutical formulation contains about 68% of a spray-dried solid dispersion.

The pharmaceutical formulation of the invention can be administered in either single or multiple doses via oral administration. Administration can be via solution, suspension, emulsion, capsule, tablet, or the like. In one embodiment, the formulation is in the form of a tablet. In a further embodiment, the formulation is in the form of a capsule.

The pharmaceutical formulation of the present invention can further be film-coated. The film-coating contains film-forming polymers and one or more coating additives. Suitable film-forming polymers include a cellulose derivative (e.g., methyl cellulose, hydroxymethyl cellulose, hydroxyethyl cellulose, hydroxypropyl cellulose, hydroxymethylethyl cellulose, hydroxypropylmethyl cellulose, sodium carboxymethyl cellulose, and ethyl cellulose), a vinyl polymer, an acrylic polymer, and a combination thereof.

In one embodiment, the pharmaceutical formulation is formulated in a unit dosage or pharmaceutical dosage form. The term "unit dosage form" or "pharmaceutical dosage form" refers to a physically discrete unit suitable as a unitary dosage for human and other mammals, each unit containing a predetermined quantity of active material calculated to produce the desired therapeutic effect, in combination with a suitable pharmaceutical ingredient. The compounds of formula (I) are generally administered in a pharmaceutically effective amount. The pharmaceutical dosage form typically contains a compound of formula (I) in an amount of about 50 to about 400 mg, (e.g., about 75 to about 375 mg, about 100 to about 350 mg, about 150 to about 325 mg, about 200 to about 300 mg, about 225 to about 270 mg, about 225 to about 250 mg, and about 50 to about 250 mg). In some embodiments, the pharmaceutical dosage form contains a compound of formula (I) in an amount of about 50 mg, about 100 mg, about 150 mg, about 200 mg, about 250 mg, about 300 mg, or about 315 mg. It will be understood, however, that the amount of the compound actually administered usually will be determined by a physician, in the light of the relevant circumstances, including the condition to be treated, the chosen route of administration, the actual compound administered and its relative activity, the age, weight and response of the individual patient, the severity of the patient's symptoms, and the like.

In one embodiment, the pharmaceutical formulation, or alternatively, the unit dosage form contains about 100 mg of a compound formula (I) formulated in a spray-dried solid dispersion having a compound:polymer ratio of 1:1.5 and the spray-dried solid dispersion is present in an amount of about 68.5% w/w.

The term "about" refers to the indicated value of the variable and to all values of the variable that are within the experimental error of the indicated value or within 10 percent of the indicated value.

The term "effective amount" refers to the amount of an active compound of this invention that is required to confer a therapeutic effect on the treated subject.

The term "substantially amorphous" refers to a composition in which greater than about 70%, or greater than about 75%, or greater than about 80%, or greater than 85%, or greater than 90%, or greater than 95%, or greater than 99% of the compound present in amorphous.

In one embodiment, the present invention provides a pharmaceutical formulation comprising the spray-dried solid dispersion which contains a pharmaceutically active ingredient and a polymer, and one or more pharmaceutically acceptable excipients or additives known in the art for oral administration. The pharmaceutical formulation can be prepared into conventional dosage forms, such as powders, granules, tablets, soft or hard capsules, or coated forms. For example, the solid dispersion in the form of powder or granules can be put into the capsules, or it can be pressed into tablets.

Still within the scope of this invention is a method of preparing the spray-dried solid dispersion described above.

To reiterate from above, the preparation method includes steps of mixing the compound and the pharmaceutically acceptable polymer in a solvent to provide a feeder solution and spray-drying the feeder solution to afford a spray-dried solid dispersion.

The solid dispersion can be prepared from a variety of forms of a compound formula (I), e.g., crystalline forms, amorphous form, pharmaceutical acceptable salts thereof, solvates, and free base.

The spray-dried solid dispersion thus prepared contains the compound of formula (I) that is substantially in an amorphous state and dispersed within a polymer matrix formed by a pharmaceutically acceptable polymer.

Advantages of the spray-dried solid dispersion of this invention include better dissolution performance, acceptable disintegration time and drug release profiles for formulation, improved dissolution/solubility for manufacturability, and improved bioavailability.

Further covered by this invention is a method of treating HCV infection by administering to a subject (e.g., a human) in need thereof a pharmaceutical formulation containing the spray-dried solid dispersion thus prepared.

In some embodiments, the solid dispersion, pharmaceutical formulation, or unit dosage form is administered, either alone or in combination with one or more therapeutic agents for treating HCV infection. These therapeutic agents can be HCV NS5A inhibitors, HCV NS5B inhibitors, HCV NS4B inhibitors, HCV p7 inhibitors (e.g., BIT225), or other antiviral agents and immunomodulatory agents (e.g., CD81 inhibitors and cyclophilin inhibitors).

Examples of HCV NS5A inhibitors include Daclatasvir (BMS-790025), Ledipasvir (GS-5885), Ombitasvir (ABT-267), GSK2336805, PPI-461, PPI-668, ACH-2928, ACH-3102, GS-5816, BMS824393, Samatavir, Elbasvir (MK-8742), and Yimitasvir (DAG-181).

Examples of HCV NS5B inhibitors include Sofosbuvir (PSI-7977), Tegobuvir, Filibuvir (PF-00868554), BMS-791325, VX-135, Lomibuvir (VX-222), VX-759, ANA598, Dasabuvir (ABT-333), ABT-072, Deleobuvir (BI-207127), IDX375, Mericitabine (RG7128), RG7432, Setrobuvir (RG7790) PSI-7851, PSI-352938, PSI-661, TMC 649128, IDX184, INX-08189, JTK-853, VCH-916, BILB 1941, GS-6620, GS-9669, and Mencitabine.

Examples of HCV NS4B inhibitors include Clemizole and GS-9132.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. The publications cited herein are incorporated by reference in their entirety.

Example 1: Synthesis of Compounds of Formula (I)

14 Compounds of formula (I), i.e., Compounds 1-14, were prepared by following the synthetic route shown in Scheme 1 above and the protocols reported in Liu et al., U.S. Pat. No. 8,389,560.

Shown below are mass spectrum (MS) and nuclear magnetic resonance of Compounds 1-14.

Compound 1: MS: m/z 906.3 ($M^+$+1); $^1$H NMR (CDCl$_3$) δ 10.18 (s, 1H), 8.62 (d, 2H), 8.25 (d, 1H), 7.78 (d, 2H), 7.70-7.61 (m, 2H), 7.55-7.46 (m, 1H), 7.01 (1H), 6.18 (1H), 5.71 (q, 1H), 5.12 (d, 1H), 5.02 (dd, 1H), 4.77 (dd, 1H), 4.64 (d, 1H), 4.53-4.43 (1H), 4.31-4.18 (m, 2H), 2.83-2.44 (m, 3H), 2.28 (q, 1H), 1.95-1.22 (m, 23H), 0.83 (s, 3H).

Compound 2: MS: m/z 895.2 ($M^+$+1); $^1$H NMR (CDCl$_3$) δ 10.45 (s, 1H), 8.60 (d, 2H), 8.22 (d, 1H), 7.55 (d, 2H), 7.67-7.60 (m, 2H), 7.45 (dd, 1H), 7.20 (s, 1H), 6.12 (s, 1H), 5.65 (q, 1H), 5.13 (d, 1H), 4.97 (dd, 1H), 4.81-4.71 (m, 2H), 4.14-4.10 (m, 2H), 2.82-2.45 (m, 3H), 2.27 (q, 1H), 1.97-1.21 (m, 14H), 1.08 (s, 9H), 0.89-0.80 (m, 4H).

Compound 3: MS: m/z 883.4 ($M^+$+1); $^1$H NMR (CDCl$_3$) δ 10.42 (s, 1H), 8.43 (d, 2H), 8.23 (d, 1H), 7.61-7.39 (m, 4H), 7.03 (d, 2H), 6.18 (s, 1H), 5.71 (q, 1H), 5.30 (d, 1H), 4.96 (dd, 1H), 4.79-4.57 (m, 4H), 4.41-4.22 (m, 1H), 4.15-4.08 (m, 1H), 2.96-2.67 (m, 3H), 2.57-2.42 (m, 1H), 2.25 (q, 1H), 1.98-0.87 (m, 29H).

Compound 4 (test compound): MS: m/z 897.4 ($M^+$+1); $^1$H NMR (CDCl$_3$) δ 10.31 (s, 1H), 8.42 (d, 2H), 8.21 (d, 1H), 7.57-7.25 (m, 4H), 7.02 (d, 2H), 6.14 (s, 1H), 5.67-5.64 (m, 1H), 5.40 (d, 1H), 5.03-4.93 (m, 1H), 4.79-4.54 (m, 4H), 4.39-4.12 (m, 2H), 2.77-2.72 (m, 2H), 2.54 (br, 1H), 2.26 (q, 1H), 2.03-1.24 (m, 29H), 0.80 (s, 3H).

Compound 5: MS: m/z 915.2 ($M^+$+1); $^1$H NMR (CDCl3) δ 10.29 (s, 1H), 8.38 (d, 2H), 7.74 (d, 1H), 7.57-7.24 (m, 3H), 7.27 (d, 2H), 6.14 (s, 1H), 5.66 (q, 1H), 5.32 (d, 1H), 4.98 (dd, 1H), 4.76 (dd, 1H), 4.71-4.48 (m, 3H), 4.39-4.08 (m, 2H), 2.85-2.42 (m, 3H), 2.31 (q, 1H), 2.03-1.24 (m, 29H), 0.80 (s, 3H).

Compound 6: MS: m/z 901.2 ($M^+$+1); $^1$H NMR (CDCl$_3$) δ 10.42 (s, 1H), 8.46 (d, 2H), 7.82 (d, 1H), 7.54 (dd, 1H), 7.42 (s, 1H), 7.32 (m, 1H), 6.98 (d, 2H), 6.14 (s, 1H), 5.65 (q, 1H), 5.33 (d, 1H), 4.97 (dd, 1H), 4.76 (dd, 1H), 4.71-4.50 (m, 3H), 4.41-4.08 (m, 2H), 2.93-2.42 (m, 4H), 2.31 (q, 1H), 2.03-0.80 (m, 29H).

Compound 7: MS: m/z 885.3 ($M^+$+1); $^1$H NMR (CDCl$_3$) δ 10.26 (s, 1H), 8.42 (d, 2H), 8.23 (d, 1H), 7.58 (m, 2H), 7.44 (m, 1H), 7.22 (s, 1H), 7.01 (d, 2H), 6.17 (s, 1H), 5.67 (q, 1H), 5.16 (d, 1H), 4.98 (dd, 1H), 4.75 (dd, 1H), 4.62 (m, 2H), 4.38-4.08 (m, 2H), 2.80-2.42 (m, 3H), 2.32 (q, 1H), 1.96-1.20 (m, 21H), 1.13 (s, 9H), 0.81 (m, 3H).

Compound 8: MS: m/z 923.2 (M$^+$+1).

Compound 9: MS: m/z 882.5 (M$^+$+1).

Compound 10: MS: m/z 881.4 (M$^+$+1); $^1$H NMR (CDCl$_3$) δ 10.47 (s, 1H), 8.40 (d, 2H), 8.23 (d, 1H), 7.76 (s, 1H), 7.62-7.41 (m, 5H), 6.13 (s, 1H), 5.65 (q, 1H), 5.33 (d, 1H), 5.03-4.87 (m, 2H), 4.78 (dd, 1H), 4.57 (d, 1H), 4.38-4.04 (m, 2H), 2.95-2.43 (m, 4H), 2.21 (q, 1H), 2.01-1.37 (m, 20H), 1.33 (s, 9H), 1.21-0.86 (m, 3H).

Compound 11: MS: m/z 895.4 (M$^+$+1); $^1$H NMR (CDCl$_3$) δ 10.30 (s, 1H), 8.40 (d, 2H), 8.23 (d, 1H), 7.59-7.43 (m, 5H), 6.98 (d, 1H), 6.16 (s, 1H), 5.65 (q, 1H), 5.41 (d, 1H), 4.98 (dd, 1H), 4.79 (q, 1H), 4.62-4.52 (m, 1H), 4.36-4.09 (m, 3H), 2.75 (brs, 2H), 2.59-2.56 (m, 1H), 2.28 (q, 1H), 1.91-1.18 (m, 31H), 0.89-0.78 (m, 4H).

Compound 12: MS: m/z 869.4 (M$^+$+1); $^1$H NMR (CDCl$_3$) δ 10.41 (s, 1H), 8.42 (d, 2H), 8.23 (d, 1H), 7.62-7.43 (m, 5H), 7.44 (dd, 1H), 6.17 (s, 1H), 5.64 (q, 1H), 5.17 (d, 1H), 4.97 (dd, 1H), 4.77-4.63 (m, 2H), 4.21-4.10 (m, 2H), 2.94-2.55 (m, 4H), 2.27 (q, 1H), 1.89-1.15 (m, 23H), 1.10 (s, 9H), 0.98-0.87 (m, 1H).

Compound 13: MS: m/z 925.4 (M$^+$+1); $^1$H NMR (CDCl$_3$) δ 10.28 (s, 1H), 8.37 (d, 2H), 8.03 (d, 1H), 7.50 (d, 2H), 7.48 (s, 1H), 7.01-6.92 (m, 2H), 6.13 (s, 1H), 5.65 (q, 1H), 5.39 (d, 1H), 4.98 (dd, 1H), 4.88 (dd, 1H), 4.64 (s, 1H), 4.53 (d, 1H), 4.41-4.23 (m, 1H), 4.19-4.11 (m, 1H), 3.88 (s, 3H), 2.78-2.42 (m, 3H), 2.26 (q, 1H), 2.04-1.18 (m, 31H), 0.89-0.78 (m, 4H).

Compound 14: MS: m/z 925.4 (M$^+$+1); $^1$H NMR (CDCl$_3$) δ 10.23 (s, 1H), 8.35 (d, 2H), 7.77 (d, 1H), 7.48 (d, 2H), 7.38-7.22 (m, 1H), 7.04-6.81 (m, 2H), 6.16 (s, 1H), 5.68 (q, 1H), 5.21 (d, 1H), 4.99 (dd, 1H), 4.78 (dd, 1H), 4.57 (d, 1H), 4.22-4.03 (m, 3H), 4.00 (s, 3H), 2.80-2.43 (m, 3H), 2.31 (q, 1H), 1.96-1.20 (m, 31H), 0.95-0.78 (m, 4H).

Example 2: Preparation and Evaluation of Solid Dispersions

The solid dispersions of the present invention were prepared by a spray-dried method well known in the art. For example, see Singh et al., Advanced Drug Delivery Reviews, 2016, 100, 27-50.

Different polymers, such as Poloxamer188, Eudragit L100, Eudragit S100, PVP VA 64, HPC-L, and PVP K30, were tested for preferred characteristics in the solid dispersion. A test compound, i.e., Compound 4, was mixed with different polymers at various ratios, and dissolved in absolute ethanol to provide a feeder solution. The solvent was removed from the feeder solution during spray-drying. The spray-dried samples thus obtained were subsequently dried in a vacuum oven to remove residual solvents that remain in the spray dried samples. After powder-blending and dry granulation, solid dispersions were produced in a tablet form or an encapsule form.

The solid dispersions described above were then tested for solubility. Each of the test solid dispersions was weighed and added to a 1.5 mL vial and then 1.0 mL of pH 6.8 USP buffer was added. The vials were shaken for 24 hours at 25° C. After equilibration for 24 hours, each mixture was centrifuged at 10,000 rpm for 10 minutes. The concentrations of the test compound under various conditions were determined by HPLC. Residual solids were collected and checked by XRPD to determine the forms of the solids.

Results are shown in Table 1 below:

TABLE 1

Solubility of different solid dispersions

| No. | Drug | Polymer | Ratio (Drug:Polymer) | Solid form | Solubility (ng/mL) |
|---|---|---|---|---|---|
| 1 | Compound 4 | — | — | Amorphous | <LOQ* |
| 2 | Compound 4 | Poloxamer 188 | 2:1 | Crystalline | 4000 |
| 3 | Compound 4 | Poloxamer 188 | 1:1 | Crystalline | 13000 |
| 4 | Compound 4 | PVP VA64 | 2:1 | Amorphous | <LOQ* |
| 5 | Compound 4 | PVP VA64 | 1:1 | Amorphous | 17000 |
| 6 | Compound 4 | PVP K30 | 2:1 | Amorphous | 8000 |
| 7 | Compound 4 | PVP K30 | 1:1 | Amorphous | 52000 |
| 8 | Compound 4 | HPC-L | 2:1 | Amorphous | 88000 |
| 9 | Compound 4 | Eudragit L100 | 2:1 | Amorphous | <LOQ* |
| 10 | Compound 4 | Eudragit L100 | 1:1 | Amorphous | <LOQ* |
| 11 | Compound 4 | Eudragit S100 | 2:1 | Amorphous | <LOQ* |

*LOQ (limit of quantification) = 621.6 ng/mL

These results indicate that the solid dispersions prepared with poloxamer 188, PVP VA 64, PVP K30, and HPC-L unexpectedly exhibited high solubility, as compared to that of poor water-soluble Compound 4.

Example 3: Effect of Compound-Polymer Ratios on the Solubility of Various Solid Dispersions Three polymers, i.e., HPC-L, PVP K30, and HPC-SSL, were used to examine the equilibrium solubility of solid dispersions when the weight ratio of Compound 4 to polymer was adjusted to 1:2. Components of HPC-L solid dispersion, PVP K30 solid dispersion, HPC-SSL solid dispersion are summarized in Table 2 below.

TABLE 2

Solid dispersions containing different polymers

| Item | HPC-L | PVP K30 | HPC-SSL |
|---|---|---|---|
| Compound 4 (mg) | 2000 | 2000 | 2000 |
| Polymer (mg) | 4000 | 4000 | 4000 |
| Ethanol (mL) | 200 | 200 | 200 |
| Solid dispersion weight (mg) | 3192.2 | 4006.4 | 4300 |
| Yield % | 53.20 | 66.77 | 71.67 |

The results of equilibrium solubility of solid dispersions of Table 2, carried by HPC-L, HPC-SSL, and PVP K30, are shown in Table 3 below. HPC-L solid dispersion, PVP K30 solid dispersion, and HPC-SLL dispersion all unexpectedly exhibited high equilibrium solubility in water or a pH 6.8 buffer.

TABLE 3

Equilibrium solubility of solid dispersions containing different polymers

| Item | HPC-L | PVP K30 | HPC-SSL |
|---|---|---|---|
| Water | 191000 (ng/mL) | 14000 (ng/mL) | 7000 (ng/mL) |
| pH 6.8 buffer | 91000 (ng/mL) | 12000 (ng/mL) | 62000 (ng/mL) |

Shown in Table 4 below are the formulations of two different solid dispersions, each of which has the weight ratio of compound to polymer being 1:1 or 1:1.5. After testing, these two solid dispersions also unexpectedly exerted similar and excellent dissolution properties.

TABLE 4

| | 1:1 weight ratio | 1:1.5 weight ratio |
|---|---|---|
| Compound 4 (g) | 40 | 20 |
| HPC-SSL (g) | 40 | 30 |
| Absolute Ethanol (mL) | 920 | 575 |
| Solid dispersion (g) | 53 | 35 |
| Yield (%) | 66 | 70 |

Formula of solid dispersions

Example 4: Preparation of Tablet and Capsule Formulations

The spray-dried solid dispersions described in EXAMPLE 3 above were used for preparing formulations in both a tablet form and a capsule form.

The tablet and capsule formulations were prepared by following protocols well known in the field. For example, see U.S. Pat. No. 9,345,712.

The tablet form contained the components shown in Table 5 below. The capsule form contained the components shown in Table 6 and Table 7 also below. Acceptable disintegration time and drug release profile were achieved using these two formulations.

TABLE 5

Formula of tablet (Compound 4, 100 mg)

| Ingredients | Unit formula/mg | Ratio % |
|---|---|---|
| Intra-granule | | |
| Solid dispersion (compound:HPC-SSL = 1:2) | 315 | 63 |
| Microcrystalline cellulose (MCC 101) | 100 | 20 |
| Croscarmellose sodium (CC—Na) | 30 | 6.0 |
| Sodium lauryl sulfate (SLS) | 5.0 | 1.0 |
| Magnesium stearate (MS) | 5.0 | 1.0 |
| Colloidal silicon dioxide (CSD) | 7.5 | 1.5 |
| Extra-granule | | |
| Croscarmellose sodium (CC—Na) | 30 | 6.0 |
| Magnesium stearate (MS) | 2.5 | 0.5 |
| Colloidal silicon dioxide (CSD) | 5.0 | 1.0 |
| Tablet weight (mg) | 500 | 100 |

TABLE 6

Formula of capsule (Compound 4, 50 mg)

| Ingredients | Unit formula/mg | Ratio % |
|---|---|---|
| Solid dispersion (compound:HPC-SSL = 1:2) | 157.5 | 68.11 |
| Microcrystalline cellulose (MCC 101) | 50 | 21.62 |
| Croscarmellose sodium (CC—Na) | 15 | 6.50 |
| Sodium lauryl sulfate (SLS) | 2.5 | 1.08 |
| Magnesium stearate (MS) | 2.5 | 1.08 |
| Colloidal silicon dioxide (CSD) | 3.75 | 1.62 |
| HG, capsule cize 0 | — | — |
| Net capsule filling weight (mg) | 231.25 | 100 |

TABLE 7

Formula of capsule (Compound 4, 100 mg)

| Ingredients | Unit formula/mg | Ratio % |
|---|---|---|
| Solid dispersion (compound:HPC-SSL = 1:1.5) | 250 | 68.50 |
| Microcrystalline cellulose (MCC 101) | 87.60 | 24.00 |
| Croscarmellose sodium (CC—Na) | 14.60 | 4.00 |
| Sodium lauryl sulfate (SLS) | 3.65 | 1.00 |
| Magnesium stearate (MS) | 5.485 | 1.50 |
| Colloidal silicon dioxide (CSD) | 3.65 | 1.00 |
| Capsule size 0 | | |
| Capsule weight (mg) | 365 | 100 |

Example 5: Pharmacokinetics of Different Formulations in Dogs

A comparative in vivo study was performed to determine the plasma pharmacokinetics of Compound 4 in two formulations as follows.

The in vivo pharmacokinetic study was conducted in five male beagle dogs after oral administration of tablet and capsule formulations each at 100 mg/animal to the dogs. There was at least a 7-day washout period between each of two phases. Dogs in phase 1 were administered Compound 4 orally in the tablet form (formula shown in Table 5) at a nominal dosage of 100 mg/animal. Dogs in phase 2 were administered Compound 4 orally in the capsule form (formula shown in Table 6) at a nominal dosage of 100 mg/animal. Blood samples were collected at pre-dose (0) and at 0.5, 1, 2, 3, 4, 6, 8, 12, 24, 36, 48, and 72 hours post administration. Plasma concentrations of Compound 4 were determined by the LC-MS/MS method. A graph of plasma concentration vs. time is shown in FIG. 1.

The results indicate that both the solid dispersion tablet and capsule formulations unexpectedly exhibited high bioavailability.

Other Embodiments

All of the features disclosed in this specification may be combined in any combination. Each feature disclosed in this specification may be replaced by an alternative feature serving the same, equivalent or similar purpose. Thus, unless expressly stated otherwise, each feature disclosed is only an example of a series of equivalent or similar features.

From the above description, one skilled in the art can easily ascertain the essential characteristics of the present invention, and without departing from the spirit and scope thereof, can make various changes and modifications of the invention to adapt it to various usage and conditions. Thus, other embodiments are also within the scope of the following claims.

The invention claimed is:
1. A spray-dried solid dispersion, comprising:
(a) a pharmaceutical compound of formula (I) shown below or a pharmaceutically acceptable salt thereof,

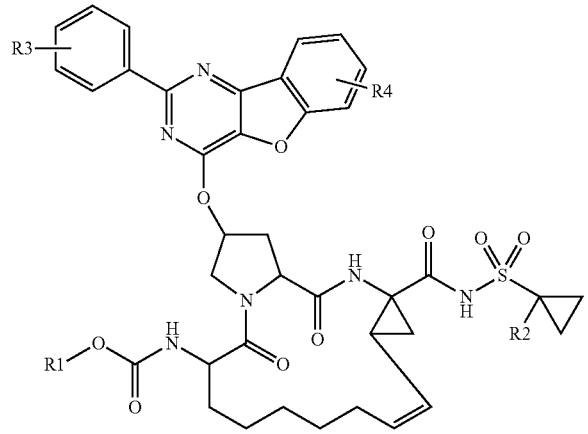

(I)

wherein
R1 is H, $C_{1-6}$ alkyl, $C_{3-10}$ cycloalkyl, $C_{3-10}$ heterocycloalkyl, aryl, or heteroaryl, each of $C_{1-6}$ alkyl, $C_{3-10}$ cycloalkyl, $C_{3-10}$ heterocycloalkyl, aryl, and heteroaryl being optionally mono-, di-, or tri-substituted with halo, nitro, cyano, amino, $C_{1-6}$ alkyl, $C_{1-6}$ alkoxyl, $C_{2-6}$ alkenyl, $C_{2-6}$ alkynyl, aryl, or heteroaryl;
R2 is H, halo, or $C_{1-6}$ alkyl;
R3 is H, halo, nitro, cyano, amino, $C_{1-6}$ alkyl, $C_{1-6}$ alkoxyl, $C_{2-6}$ alkenyl, $C_{2-6}$ alkynyl, $C_{3-10}$ cycloalkyl, $C_{3-10}$ heterocycloalkyl, aryl, or heteroaryl, or R3 is fused with phenyl to form a bicycle, each of amino, $C_{1-6}$ alkyl, $C_{1-6}$ alkoxyl, $C_{2-6}$ alkenyl, $C_{2-6}$ alkynyl, aryl, and heteroaryl being optionally mono-, di-, or tri-substituted with halo; and
R4 is H, halo, nitro, cyano, amino, $C_{1-6}$ alkyl, $C_{1-6}$ alkoxyl, $C_{2-6}$ alkenyl, $C_{2-6}$ alkynyl, $C_{3-10}$ cycloalkyl, $C_{3-10}$ heterocycloalkyl, aryl, or heteroaryl, each of amino, $C_{1-6}$ alkyl, $C_{1-6}$ alkoxyl, $C_{2-6}$ alkenyl, $C_{2-6}$ alkynyl, $C_{3-10}$ cycloalkyl, $C_{3-10}$ heterocycloalkyl, aryl, and heteroaryl being optionally mono-, di-, or tri-substituted with halo, nitro, cyano, amino, $C_{1-6}$ alkyl, $C_{1-6}$ alkoxyl, $C_{2-6}$ alkenyl, $C_{2-6}$ alkynyl, aryl, or heteroaryl, and
(b) a pharmaceutically acceptable polymer, the pharmaceutical compound being dispersed in a polymer matrix formed from the pharmaceutically acceptable polymer, wherein the weight ratio of the pharmaceutical compound to the pharmaceutically acceptable polymer is from 4:1 to 1:4, and the pharmaceutically acceptable polymer is poloxamer, polyvinylpyrrolidone, or hydroxypropylcellulose.

2. The spray-dried solid dispersion of claim 1, wherein R1 is $C_{1-6}$ alkyl or $C_{3-10}$ cycloalkyl and R2 is H or $C_{1-6}$ alkyl.

3. The spray-dried solid dispersion of claim 1, wherein R1 is $C_{1-6}$ alkyl or $C_{3-10}$ cycloalkyl; R2 is H or $C_{1-6}$ alkyl; R3 is H, halo, amino, $C_{1-6}$ alkyl, or $C_{1-6}$ alkoxyl, each of amino, $C_{1-6}$ alkyl, and $C_{1-6}$ alkoxyl being optionally mono-, di-, or tri-substituted with halo; and R4 is H, halo, $C_{1-6}$ alkyl, or $C_{1-6}$ alkoxyl.

4. The spray-dried solid dispersion of claim 1, wherein the pharmaceutical compound is one of the compounds shown below:

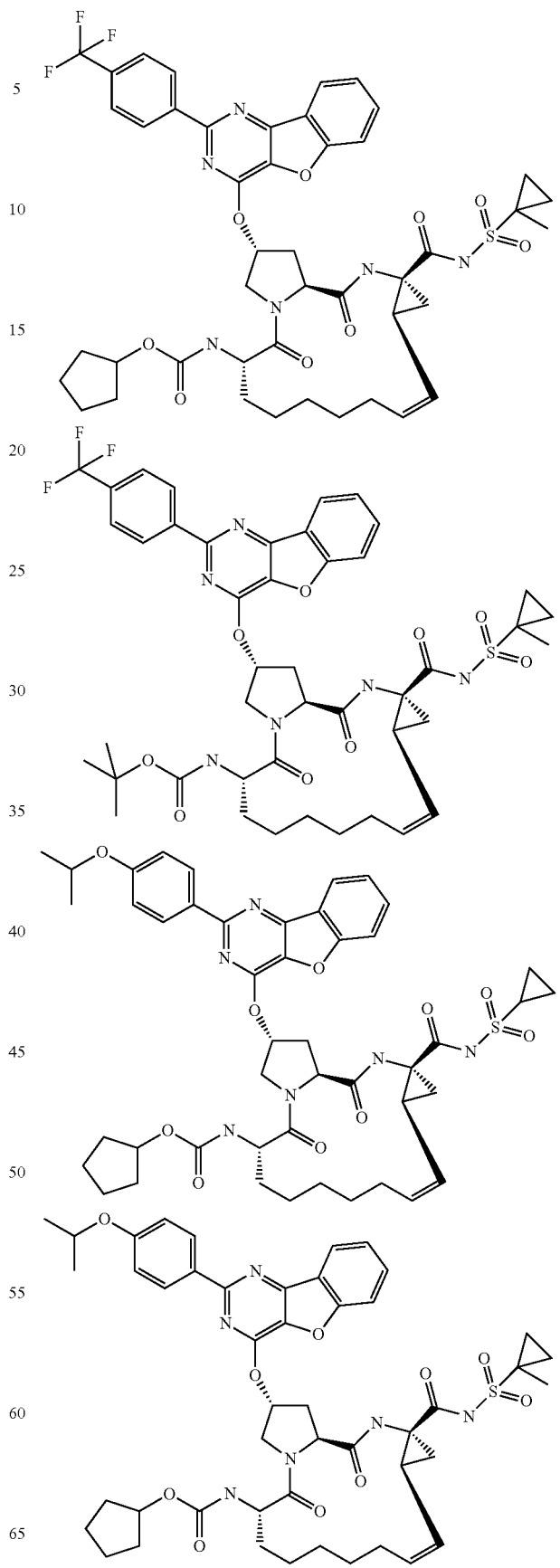

25
-continued
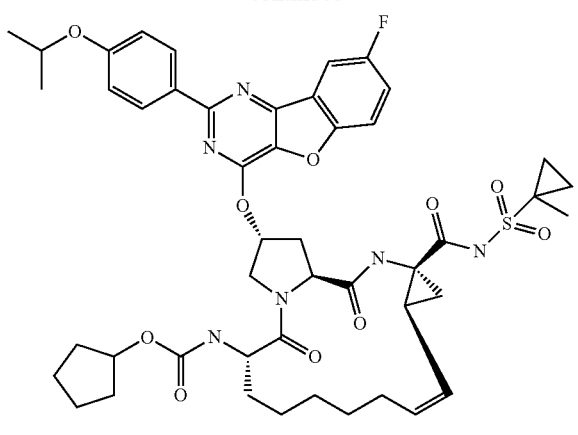
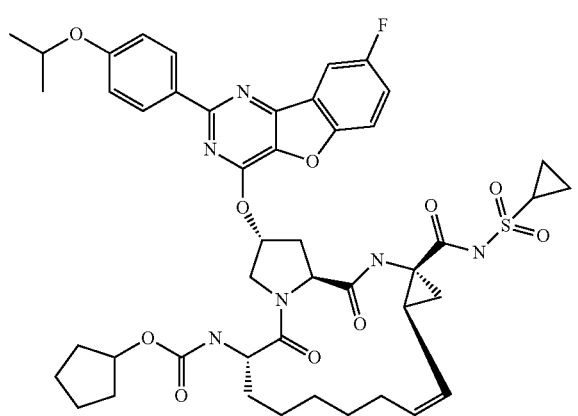
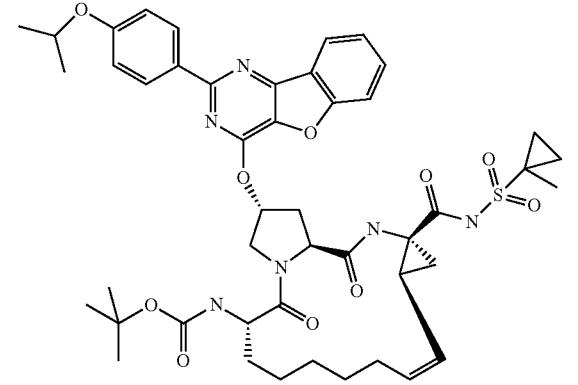
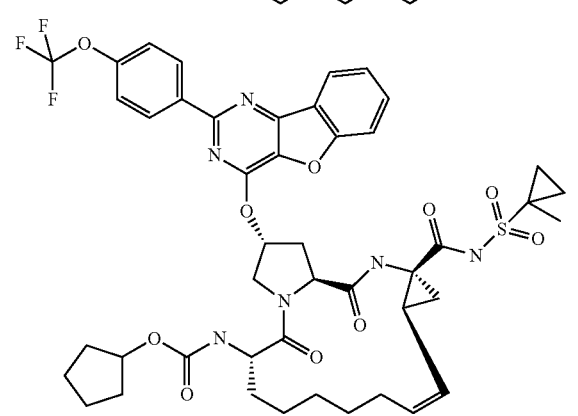
26
-continued
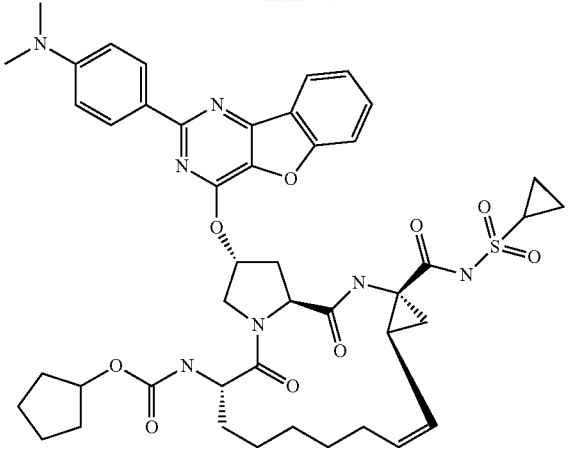

-continued

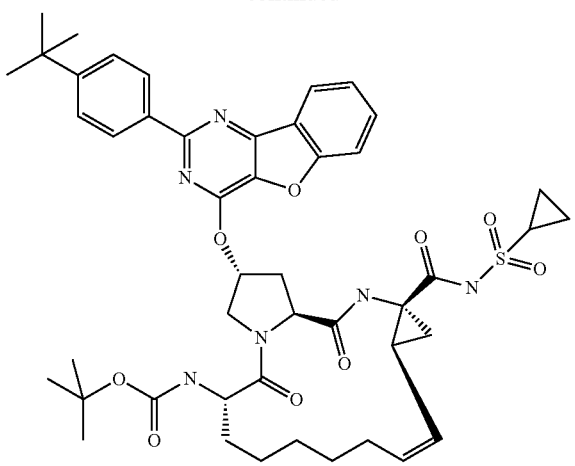

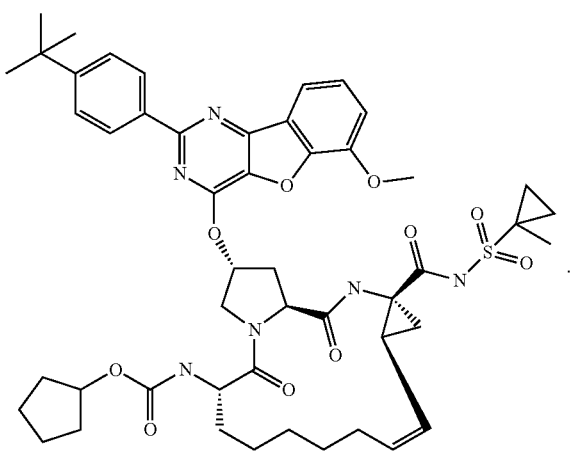

5. The spray-dried solid dispersion of claim 4, wherein the pharmaceutical compound is

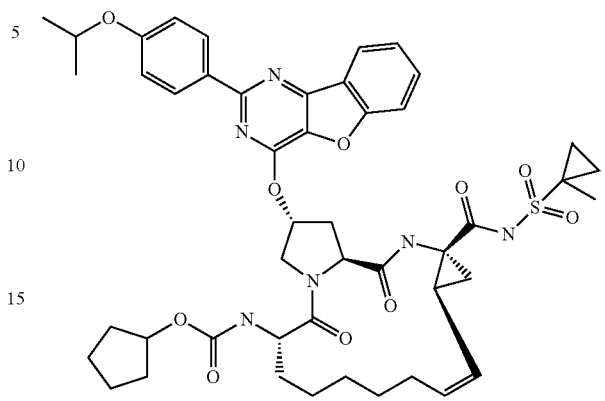

6. The spray-dried solid dispersion of claim 1, wherein the pharmaceutically acceptable polymer is poloxamer 188, PVP K30, PVP VA64, HPC-L, or HPC-SSL.

7. The spray-dried solid dispersion of claim 6, wherein the pharmaceutically acceptable polymer is PVP K30, HPC-L, or HPC-SSL.

8. The spray-dried solid dispersion of claim 7, wherein the pharmaceutically acceptable polymer is HPC-SSL.

9. The spray-dried solid dispersion of claim 1, wherein the weight ratio of the pharmaceutical compound to the pharmaceutically acceptable polymer is from 2:1 to 1:2.

10. The spray-dried solid dispersion of claim 9, wherein the weight ratio of the pharmaceutical compound to the pharmaceutically acceptable polymer is 1:1.

11. The spray-dried solid dispersion of claim 9, wherein the weight ratio of the pharmaceutical compound to the pharmaceutically acceptable polymer is 1:1.5.

12. The spray-dried solid dispersion of claim 1, wherein the pharmaceutical compound is substantially amorphous.

13. A pharmaceutical formulation comprising a spray-dried solid dispersion of claim 1 and optionally one or more pharmaceutical acceptable ingredients selected from the group consisting of one or more diluents, one or more disintegrants, one or more binders, one or more lubricants, one or more glidants, and one or more surfactants.

14. The pharmaceutical formulation of claim 13, wherein the spray-dried solid dispersion is present at 30% to 80% w/w.

15. The pharmaceutical formulation of claim 14, wherein the spray-dried solid dispersion is present at 60% to 70% w/w.

16. The pharmaceutical formulation of claim 15, wherein the pharmaceutical compound is

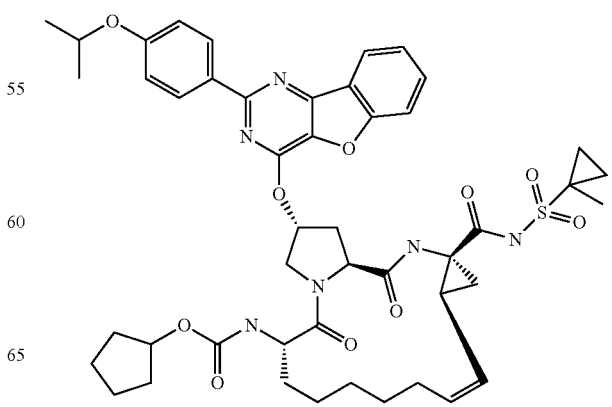

and the weight ratio of the pharmaceutical compound to the pharmaceutically acceptable polymer is from 2:1 to 1:2.

17. The pharmaceutical formulation of claim 13, wherein the formulation is produced in unit dosage form and contains 50 to 400 mg of the pharmaceutical compound.

18. The pharmaceutical formulation of claim 17, wherein the formulation contains 50 to 250 mg of the pharmaceutical compound.

19. The pharmaceutical formulation of claim 18, wherein the formulation contains 50 mg of the pharmaceutical compound.

20. The pharmaceutical formulation of claim 18, wherein the formulation contains 100 mg of the pharmaceutical compound.

21. The pharmaceutical formulation of claim 13, wherein the one or more pharmaceutical acceptable ingredients are selected from the group consisting of microcrystalline cellulose, croscarmellose sodium, sodium lauryl sulfate, magnesium stearate, and colloidal silicon dioxide.

22. The pharmaceutical formulation of claim 13, wherein the pharmaceutical formulation is in tablet form.

23. The pharmaceutical formulation of claim 13, wherein the pharmaceutical formulation is in capsule form.

24. The pharmaceutical formulation of claim 13, wherein the pharmaceutical formulation contains a film-coating.

25. A method of preparing a spray-dried solid dispersion of claim 1, comprising:
  mixing the pharmaceutical compound and the pharmaceutically acceptable polymer in a solvent to provide a feeder solution, and
  spray-drying the feeder solution to afford a spray-dried solid dispersion.

26. The method according to claim 25, wherein the solvent is absolute ethanol.

27. A method of treating hepatitis C virus (HCV) infection in a human in need thereof, the method comprising administering to the human a therapeutically effective amount of a spray-dried solid dispersion of claim 1.

28. The method of claim 27, wherein the spray-dried solid dispersion is administered either alone or in combination with one or more therapeutic agents selected from the group consisting of one or more HCV NS5A inhibitors, one or more HCV NS5B inhibitors, one or more HCV NS4B inhibitors, one or more HCV p7 inhibitors, and one or more immunomodulatory agents.

29. The method of claim 28, wherein each of the one or more HCV NS5A inhibitors is Daclatasvir, Ledipasvir, Ombitasvir, GSK2336805, PPI-461, PPI-668, ACH-2928, ACH-3102, GS-5816, BMS824393, Samatavir, Elbasvir, or Yimitasvir; each of the one or more HCV NS5B inhibitors is Sofosbuvir, Tegobuvir, Filibuvir, BMS-791325, VX-135, Lomibuvir, VX-759, ANA598, Dasabuvir, ABT-072, Deleobuvir, IDX375, Mericitabine, RG7432, Setrobuvir, PSI-7851, PSI-352938, PSI-661, TMC 649128, IDX184, INX-08189, JTK-853, VCH-916, BILB 1941, GS-6620, GS-9669, or Mencitabine; each of the one or more HCV NS4B inhibitors is Clemizole or GS-9132; and each of the one or more immunomodulatory agents is a CD81 inhibitor or a cyclophilin inhibitor.

* * * * *